United States Patent [19]

Folkenroth et al.

[11] 4,245,989
[45] Jan. 20, 1981

[54] WATER ECONOMIZING SYSTEM FOR DENTAL EQUIPMENT

[75] Inventors: Richard P. Folkenroth, Dover; Richard E. Plowman, York, both of Pa.

[73] Assignee: Dentsply Research & Development Corp., Milford, Del.

[21] Appl. No.: 55,938

[22] Filed: Jul. 9, 1979

[51] Int. Cl.³ .............................................. A61C 17/04
[52] U.S. Cl. ........................................ 433/92; 433/27; 4/263
[58] Field of Search ....................... 433/92, 95, 97, 91, 433/27, 28; 137/624.11; 4/262, 263, 224, 302, 313, 317, 318; 417/167, 196, 280; 210/127

[56] References Cited

U.S. PATENT DOCUMENTS

| | | | |
|---|---|---|---|
| 1,648,108 | 11/1927 | Brown | 4/302 |
| 2,786,210 | 3/1957 | Fraser | 4/303 |
| 3,229,368 | 1/1966 | Tocchini | 433/27 |
| 3,482,313 | 12/1969 | Stram | 433/92 |
| 3,636,974 | 1/1972 | Beguiristain | 433/92 |
| 3,656,511 | 4/1972 | Hood | 4/303 |
| 3,842,448 | 10/1974 | Kahn et al. | 4/263 |
| 3,964,112 | 6/1976 | Plowman | 433/97 |
| 4,115,879 | 9/1978 | Toms | 210/138 |
| 4,126,218 | 7/1979 | McCormick | 210/167 |
| 4,197,597 | 4/1980 | Toms | 210/138 |

Primary Examiner—Gene Mancene
Assistant Examiner—John J. Wilson
Attorney, Agent, or Firm—C. Hercus Just

[57] ABSTRACT

This invention pertains to a water recycling system for economy in water consumption by dental evacuating equipment employing a water seal type pump and includes a storage tank for waste water received from the pump, a fresh water tank above the storage tank, and an air and water separator compactly arranged with said tanks, passage means between said tanks to permit makeup and flushing water to pass from the fresh water tank to the storage tank and flush the latter through syphon mechanism, except residual seal water remaining in the pump. Conduits extend from dental evacuating equipment to the pump and then to the air and water separator to vent air to atmosphere and pass waste water to the storage tank, and an additional waste water conduit extends in gravity-flow manner from the storage tank back to the pump for recycling and economy in water consumption. Timer mechanism effects discharge of the waste water to sewer from the storage tank after non-use of the pump for a predetermined period of time, such as at the end of the day, fresh water then also being discharged to said storage tank from the fresh water tank to purge the same and prepare for re-filling with fresh water at the commencement of operation the next day.

4 Claims, 12 Drawing Figures

WATER ECONOMIZING SYSTEM FOR DENTAL EQUIPMENT

BACKGROUND OF THE INVENTION

Prior to the past twenty years, dental handpieces, commonly known as drills, operated at a speed of around 8000 to 10,000 rpm and no cooling of such drilling operation existed to any substantial extent. Dental cuspidors also were stationary at one side of the dental chair and flushing water for the same was connected to the office water system and usually employed a continuous stream of water. The only water that usually entered the patient's mouth up to that time was what the dentist squirted into the mouth by way of a syringe for purposes of flushing material removed by the dental handpiece and otherwise.

With the advent of so-called high speed dentistry about twenty years ago, which included the use of so-called dental drills that operated at speeds of 400,000 rpm or more, it was found to be desirable and even necessary to accompany such drilling with a spray of water that continuously flushed the material removed from teeth and the like by the dental handpiece. The amount of water thus discharged required the development of apparatus to rapidly remove the water and debris from the oral cavity and this gave rise to the advent of so-called high-volume evacuation. At that time, however, dental cuspidors of the aforementioned conventional type remained in use and even at present, many dental operatories still employ the same. In addition, saliva ejectors have been used for many years and are still used at present for purposes of removing emissions from the salivary glands which occurs during the time a dentist is working in the oral cavity and vacuum means were, and are, still used to operate such saliva ejectors.

For purposes of providing vacuum in the aforementioned high-volume evacuators and saliva ejectors, as well as certain new forms of cuspidors which are hand-held by the patient, and from which expectoration is removed by vacuum, it has been somewhat common practice to employ mechanism such as the equivalent of pot-type vacuum cleaners, which developed adequate vacuum to satisfy the needs of a limited amount of high-volume evacuators, saliva ejectors and cuspidors in dental offices, particularly if only a single or possibly two operatories were involved.

The modern tendency is for even a single dentist and certainly two or three associated dentists to utilize in many instances, a substantial number of operatories, such as of the order of four to six, or more, particularly where two or more dentists operate in the same suite of offices. To provide adequate evacuation for such an arrangement and number of offices and operatories, more effective means than the capabilities of the pot-type vacuum cleaners to provide vacuum service, now are required.

By way of illustration of evacuation apparatus of the type employing pot-type vacuum cleaner units or the like, attention is directed to prior U.S. Pat. Nos. 2,784,717 to Thompson, dated Mar. 12, 1957, and 3,138,837 to Bishop, dated June 30, 1964. For providing more effective evacuation and capable of being produced by such devices, some evacuating systems including the use of liquid seal pumps were devised and an early example of this type of pump in an oral vacuum system comprises the subject matter of prior U.S. Pat. No. 3,482,313 to Stram, dated Dec. 9, 1969, in which a single liquid seal pump is employed for purposes of supplying vacuum to a high-volume evacuator, a saliva ejector, and a dental cuspidor of the hand-held type, which cuspidor also is provided with flushing water, the removal of which likewise is required by the vacuum system. In said systems, fresh water from the city supply, for example, is continuously fed to the vacuum pump for purposes of maintaining the liquid seal therein that is essential to the effective operation thereof, the water then passing from the pump to a sewer connection. In some installations resulting from the development of said Stram patent, evacuation systems, including a plurality of such liquid seal pumps, have been developed to provide a greater amount of vacuum power, such as the plurality of pumps included in the system comprising the subject matter of prior U.S. Pat. No. 3,964,112 to Plowman, dated June 22, 1976. It readily can be visualized that in systems employing plural pumps of the type referred to require the use of very substantial quantities of water during a single day, for example, and situations are quite common where anywhere from 25 to 90 gallons per hour are known, especially where a number of high-volume evacuators are employed and the water is discharged directly to sewer means from said pumps.

In order to economize in such consumption rates of water, previous efforts have been made to provide evacuating systems with liquid conduit circuitry, filter means, sediment tanks, pressure tanks requiring auxiliary pumps to circulate the liquid, and other control means, several examples of which respectively are shown in said aforementioned Plowman patent, as well as prior U.S. Pat. No. 3,842,448 to Kahn et al., dated Oct. 22, 1974. In both of these prior patents, the evacuating system primarily is concerned with removing the discharge from cuspidors of the type employing flushing water and in order to recycle the waste liquid, it was necessary to include in the system employed in said aforementioned patents, means by which blood, tooth and bone chips, and other extraneous waste material are removed from the fluid which is to be recycled through the cuspidors, said systems even requiring deodorizing means in order that the water recycled to the cuspidors would not have objectionable odors, either to the patient or the professional personnel in the operatory.

It has been found that even more effective systems are desirable, however, not only to provide greater vacuum service but even greater efficiency in recycling the waste water and utilizing even more stringent requirements of fresh water to be supplied to the system, such as of the order of consuming only 25 or 30 gallons per day, as compared with 25 to 90 gallons per hour in the old systems employing, for example, air type blowers, and earlier water pump systems, to provide the vacuum. The present invention provides such more effective and efficient system, details of which are described hereinafter.

SUMMARY OF THE INVENTION

The prime objective of the present invention is to provide an economical use of water required by dental evacuating equipment in modern operatories, particularly in multiple operatories requiring adequate vacuum to serve a plurality of evacuating equipment, such as high-volume evacuators, saliva ejectors and cuspidors, or otherwise, said system employing one or more liquid seal type pumps for maximum efficiency in producing the required degree of vacuum, the system obtaining initial supplies of water from city sources or the like but economizing in the use thereof by directing the waste water discharged from said pump into a storage tank and from which said waste liquid or water is recycled to the pump continuously during the period in which the pump is operating and also including a fresh water tank in the system, preferably mounted directly over the storage tank for waste water and including passage means between the two tanks controlled by a valve operable automatically when, for example, limited amounts of make-up water are required by the waste tank to effect maximum and efficient operation of the pump.

Another object of the invention is to include in the system referred to above, a separator unit for air and water which is received from the evacuating equipment and passed through the pump to said separating unit in order that the air drawn into the evacuating equipment by the pump may be separated from the waste water so that only the waste water is directed to the waste storage tank, conduits of adequate size for the mixture of air and water being employed between the evacuating equipment and the pump, and also between the pump and the air-water separator unit, but a conduit of much smaller size being used to pass the water from the waste storage tank to the pump, such passage preferably being by gravity flow.

A further very important object of the invention is to include a timer in the system, together with drain means for the waste storage tank, whereby after a predetermined period of time which is measured by the timer, it automatically effects emptying of the waste water tank to sewer means, such as at the end of the day, said emptying preferably occurring by syphon means and the operation thereof being effected by the discharge of fresh water from the fresh water tank into the waste water tank, whereby the head of such flow of water is sufficient to initiate the syphon action, but the system also preferably including a shut-off valve automatically in the return conduit from the waste water tank to the pump that is operable automatically under such circumstances to prevent draining the water seal in the pumps which is essential to remain therein for priming purposes the next time the pumps operate, as well as prevent water flowing from the tanks to fill pumps before flushing after vacuum is turned off.

Ancillary to the foregoing object, it is another object of this invention to include control means in the system whereby each time the evacuating equipment becomes inactive, the pump is stopped and operation of the aforementioned timer is initiated for said predetermined period but, if the pump is reactivated during that period, the timer is rendered inactive and does not again become active until the next time the pump is stopped, whereby the timer commences to measure said predetermined period for the full extent of the period, thereby insuring that the system will be drained of the waste water at least at the end of the day.

A still further object related to the foregoing object is the provision of a start-up control being operated at the beginning of any operating period, such as at the beginning of a day in the operatory, whereupon said control means causes fresh water from the city supply to fill both the waste water tank and fresh water tank to predetermined levels, which levels are controlled preferably by float switches operating a solenoid valve.

A still further object of the invention is to provide a system in which a plurality of said pumps are operated in tandem, and conduit systems associated with said pumps between the dental evacuating equipment and the pumps include a collector for solid materials to separate the same from the incoming mixture of air and water before directing the air and water to an intake manifold from which a pair of conduits respectively extend to the inlet end of the pumps and the outlet ends of the pumps are connected respectively by additional conduits to an exhaust manifold from which a single conduit extends to the air-water separator.

Relative to the foregoing object, it is a further object to enclose the system, including the pumps, in cabinetry which includes a wall having a recess extending inward therefrom and said solids collector being housed within said recess for convenient access to service personnel, the collector including a readily removable receptacle in which the solid particles are retained after being separated from the incoming mixture of water and air, whereby the solid material readily may be retrieved from said receptacle and the latter quickly being reconnected to the collector for continued use.

Details of the foregoing objects and of the invention, as well as various other objects thereof, are set forth in the following specification and illustrated in the accompanying drawings comprising a part thereof.

DETAILED DESCRIPTION OF THE PREFERRED EMBODIMENT

Figure 1:
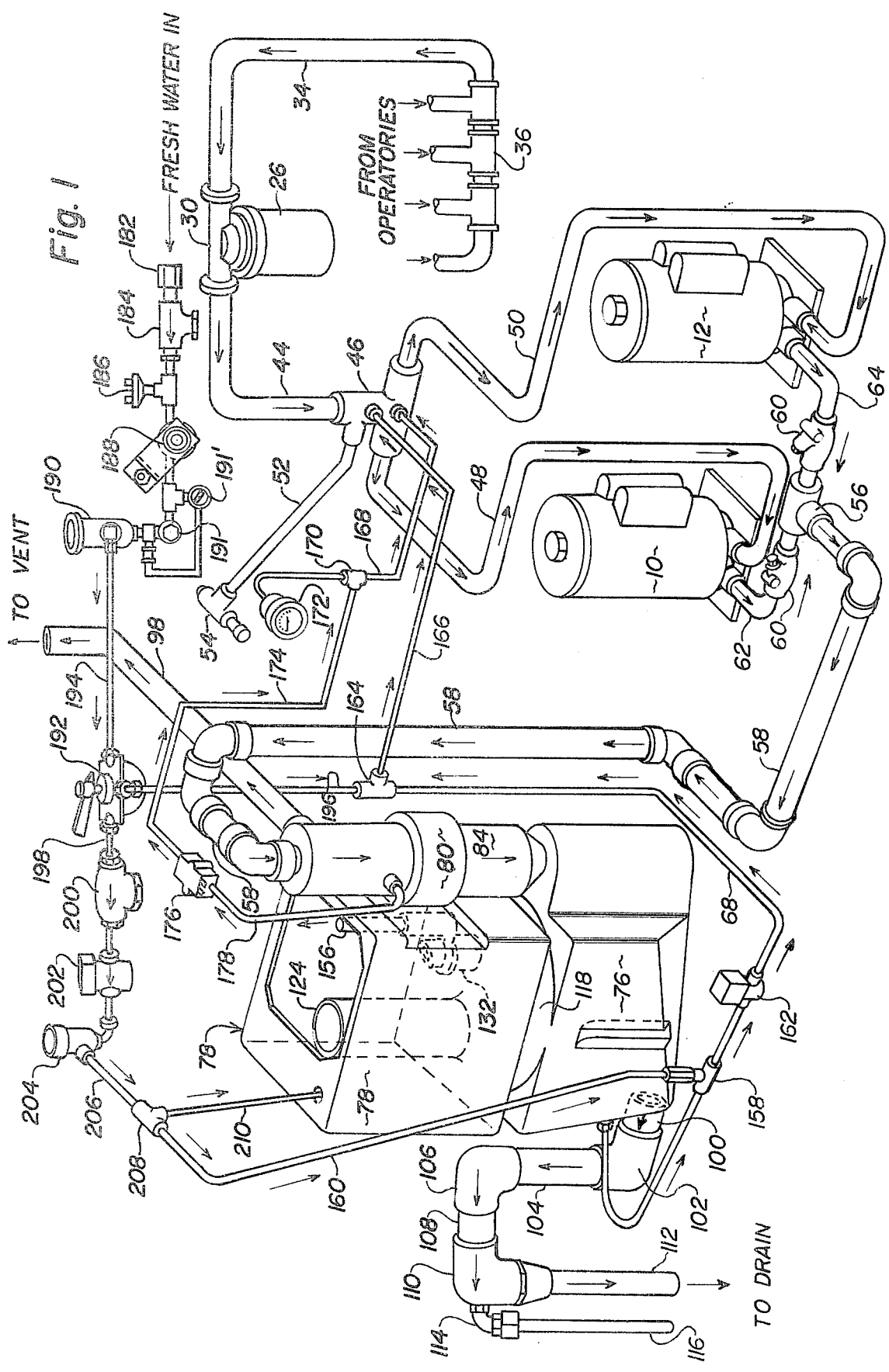
FIG. 1 is a perspective, somewhat diagrammatic layout view, showing a typical multiple pump evacuating unit connected by conduits to a waste water recycling unit and the various conduits included in the layout having direction arrows associated therewith to facilitate an understanding of the systems.

As indicated above, the present invention pertains to a system for recycling wastewater originating from dental evacuating equipment of various types and in which the pump equipment which produces vacuum in the system to withdraw said wastewater from the evacuating equipment is of the waterseal type. In conventional equipment employing waterseal type pumps, it is normal to continuously flow fresh water through said pumps for purposes of effecting the seal in said pump and thereby cause the pump to withdraw a mixture of air and water from said evacuating equipment, such as high-volume oral evacuators, cuspidors, saliva ejectors, and otherwise. Contrary to such practice, the present invention provides means by which wastewater from said evacuating equipment is discharged to storage means from which it is continuously withdrawn for recycling and recirculating through the pumps and storage means and utilizes only a very limited amount of fresh water during even an entire day of operation, thereby greatly economizing, not only in water consumption, but also in the cost of operating sewage facilities to process wastewater from dental operatories when the same is not recycled and instead is discharged continuously to a sewer system, which in most localities leads to a water treatment facility before discharging the same to a stream or the like.

Although, in a broad sense, recycling wastewater of this type is disclosed in prior U.S. Pat. No. 3,964,112, referred to hereinabove, the system comprising the present invention affords substantial improvement over the system described and claimed in said prior patent, not only by broadening the use of the liquid seal pumps to service all types of dental evacuating equipment, as distinguished simply from cuspidors, as referred to in said patent, but in addition, the system shown in said prior patent for recycling the water has been simplified in the present invention, as described in detail hereinafter.

In the recycling system of the present invention, improvements have been made not only in the recycling equipment, but also in the liquid seal pump portion of the system, and preferably, the liquid seal pump portion of the system is contained in one cabinet and the wastewater recycling equipment and system is contained in a separate cabinet, said cabinets being interconnected by appropriate conduits. The inclusion of these respective portions of the system in separate cabinets provides greater versatility with respect to the installation of the same in one or more dental operatories, especially in an establishment where a plurality of operatories are all respectively connected to the pump and recycling system for the wastewater in view of the fact that substantial vacuum capacity is normally needed in establishments of such type, wherein a number of operatories are arranged in a suite of offices, particularly those which are serviced by a number of dentists occupying such single suite of offices and operatories. Accordingly, to streamline the description of the several portions of the overall system, the following specification initially describes the liquid pump system which preferably includes a plurality of liquid seal pumps, the wastewater recycling portion of the system, and then a description of the operation of the overall system, including both the liquid seal pump portion and the water recycling portion, as follows.

LIQUID SEAL PUMP SYSTEM

Figure 2:
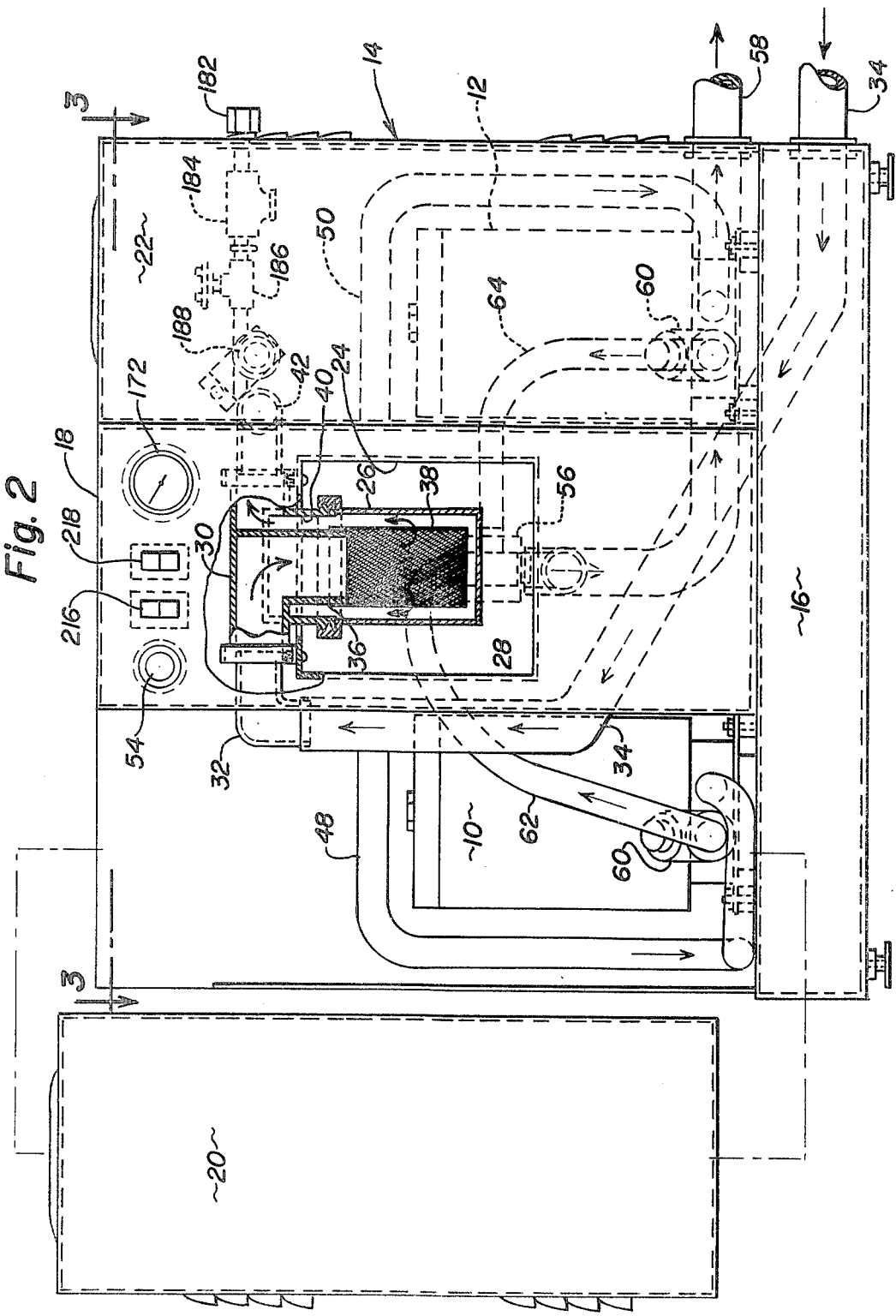
FIG. 2 is a front elevation of a cabinet in which the evacuating multiple pump system, shown in FIG. 1, is included, the cabinet at one end having removable covers mounted in place, and at the left-hand end the cover is removed to expose part of the system within said cabinet.
Figure 3:
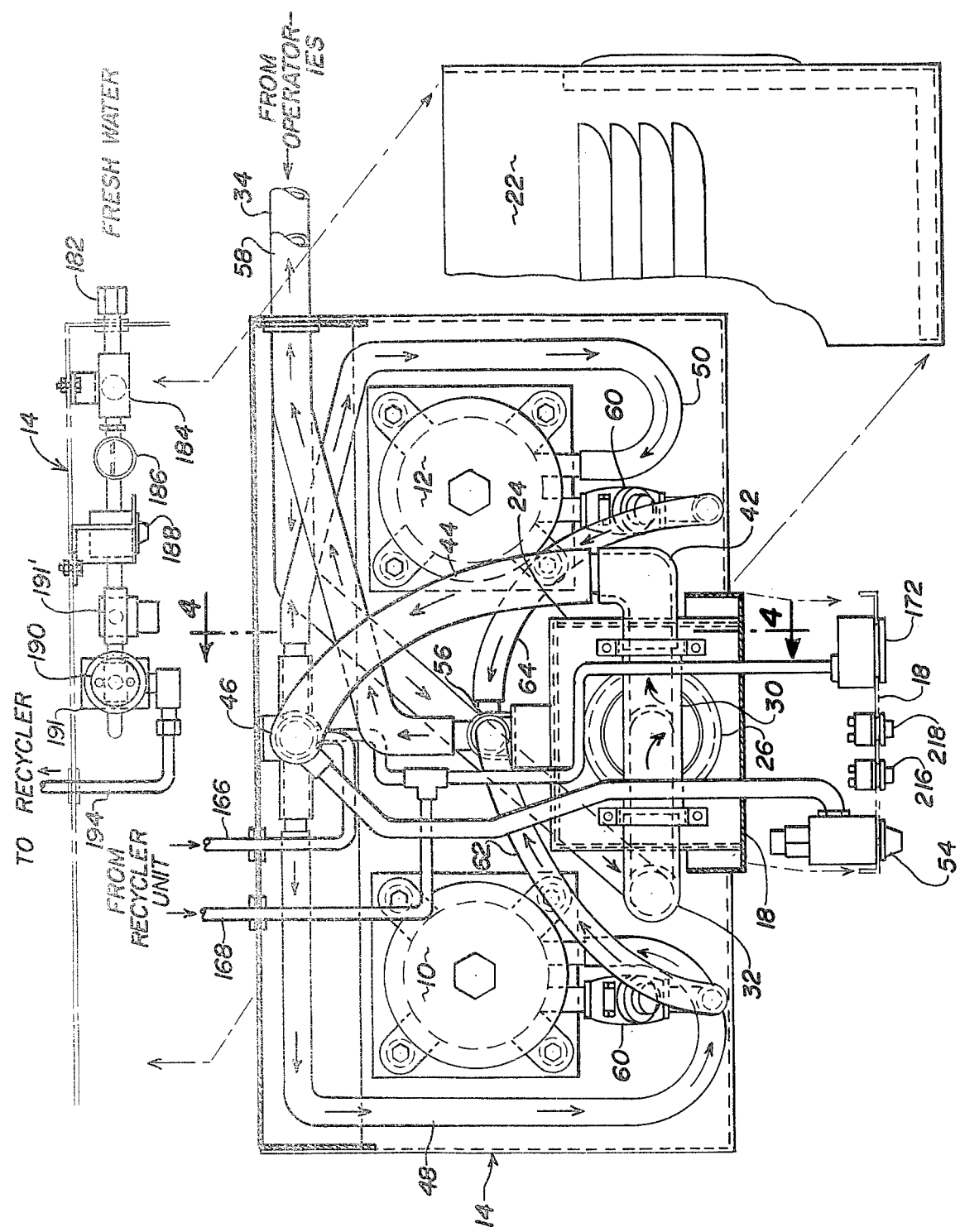
FIG. 3 is a horizontal sectional view showing in plan manner the contents of the cabinet shown in FIG. 2, as seen on the line 3—3 thereof, a portion of the top part of one of the cabinet covers being shown fragmentarily and in exploded manner in said figure, as well as part of the control means and circuitry of the system in the cabinet which overlies the illustrated equipment therein being shown above the cabinet in exploded manner.
Figure 4:
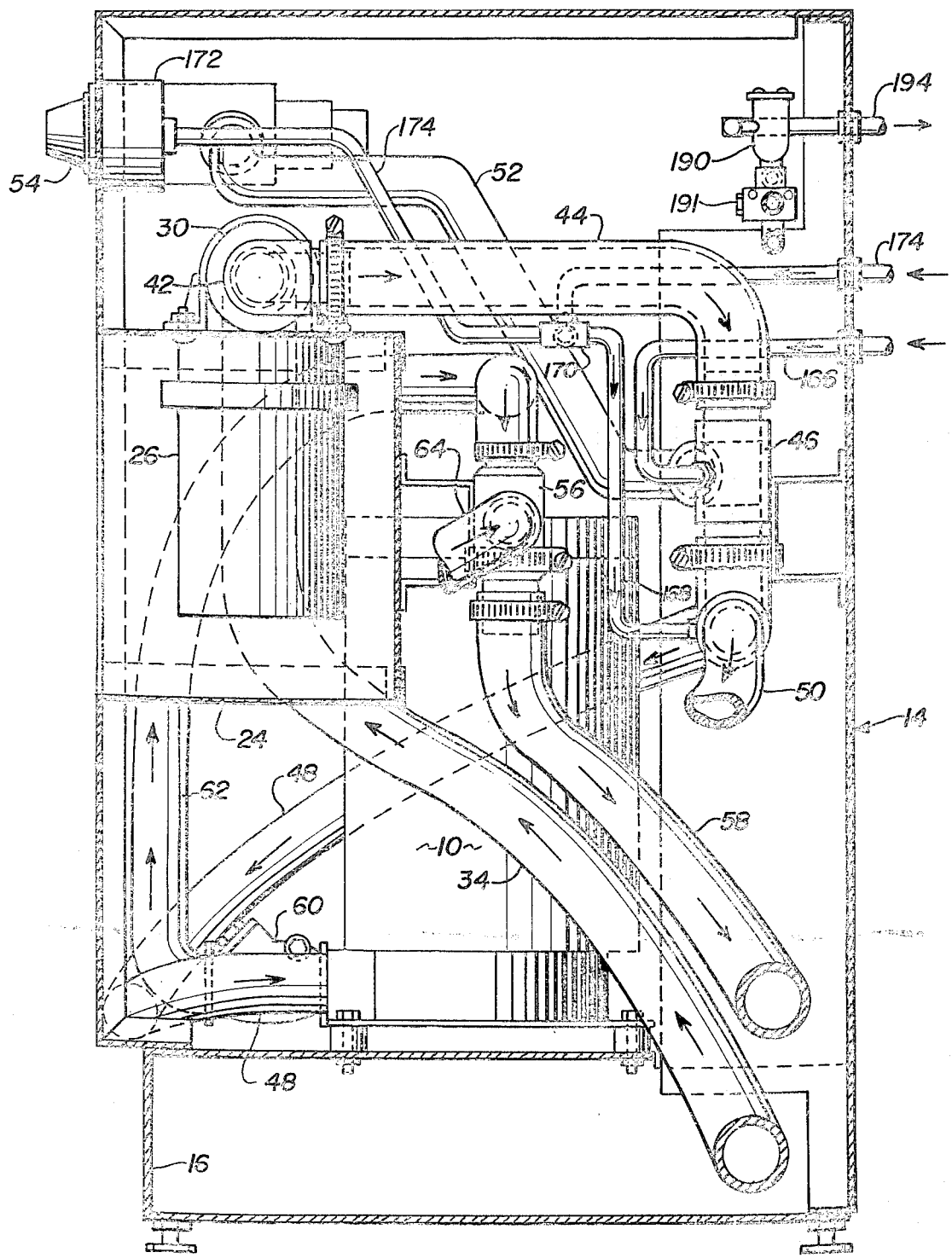
FIG. 4 is a vertical sectional view, shown on a larger scale than used in FIG. 3, and illustrating details of the contents of the cabinet shown in FIG. 3, as seen on the line 4—4 thereof.
Figure 5:
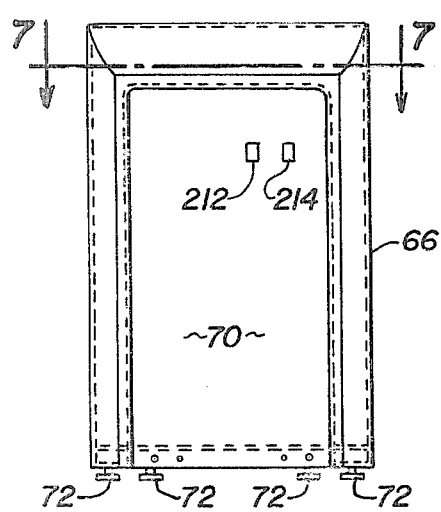
FIG. 5 is a front view of a cabinet containing the water recycling system, illustrated at the left-hand portion of FIG. 1.

Referring to the drawings, FIG. 1 illustrates somewhat diagrammatically the combined system of the present invention, including adjacent the right-hand portion thereof, the liquid seal pump portion thereof and adjacent the left-hand portion thereof, the wastewater recycling portion. The liquid seal pump portion of the overall system also is illustrated in detail in FIGS. 2-4, to which the following description pertains:

Referring to FIG. 2, it will be seen that a pair of liquid seal pumps 10 and 12 are shown respectively in opposite side portions of a cabinet 14, which comprises a base 16, a central section 18, and opposite removable side cabinet covers 20 and 22, the cover 20 being shown removed toward the left from the base portion of the cabinet, while the side cover 22 is mounted in enclosing position with respect to the cabinet 14. The central section 18 of the cabinet has an inwardly extending recess 24 within which a solids collector 26 is positioned for ready access.

The solids collector 26 comprises a cup-shaped container 28 threadably connected for quick attachment and detachment to a tee 30, one end of which is connected to an inlet elbow 32, leading by means of inlet conduit 34 which is connected to the exemplary series of discharge conduits 36, shown in FIG. 1, it being understood that any reasonable number of operatory wastewater and evacuating conduits may be interconnected to the inlet conduit 34. Said inlet conduit discharges through the elbow 32 into the inner, downwardly extending port means 36 to which the upper end of a mesh basket 38 is connected for purposes of retaining any solid particles, such as metal, bone, enamel particles, and the like to prevent the same from passing to the sewer or into the water recycling portion of the system. Said particles are separated from the incoming wastewater and said wastewater then passes into the cup 26 and upwardly into outlet passage 40 of the tee 30, which discharges into the discharge elbow 42, shown best in FIGS. 2 and 3.

The discharge elbow 42 is connected to one end of a discharge conduit 44 which discharges into intake manifold 46. Due to the fact that the inlet conduit 34 from the operatory conducts a mixture of air and water, as well as certain solid particles, the diameter of the conduits 34 and 44 are relatively large, such as the order of approximately 1½ inches, for example, and not to be considered restrictive, and said conduit also is flexible for purposes of enabling the same to be compactly arranged within the cabinet 14.

The intake manifold 46 is somewhat in the nature of a tee, the stem of the tee being connected to the discharge conduit 44, while the opposite ends of the head of the tee respectively are connected to delivery conduits 48 and 50, which respectively are connected at the opposite ends thereof to the inlet ports of liquid seal pumps 10 and 12. Also, the stem of the tee comprising the intake manifold 46 has a branch conduit 52, see FIG.

1, leading therefrom, which is connected at the outer end thereof to an adjustable vacuum control valve 54.

The pump system also includes an exhaust manifold 56, which is in the form of a tee, the stem thereof being connected to one end of a discharge conduit 58, which leads to the water recycling system, as described in detail hereinafter. The opposite ends of the head of the tee comprising exhaust manifold 56, respectively are connected to check valves 60 and discharge conduits 62 and 64 respectively leading from the discharge ports of the pumps 10 and 12.

From the foregoing, it will be seen that the pump system receives waste fluid and some debris from the dental operatories, separates the solid particles from the air and water fluids by means of the solids collector 26, and then passes the wastewater respectively to the liquid seal, high vacuum type pumps 10 and 12 which are capable of discharging jointly, or singly, if desired, substantial quantities of air and water mixture through the discharge conduit 58 to the water recycling unit, which will now be described.

WATER RECYCLING UNIT AND SYSTEM

In addition to being somewhat diagrammatically, as well as specifically illustrated in FIG. 1, the water recycling unit and system is shown in detail in FIGS. 5–9. It will be understood that in the preferred embodiment of the invention, the water recycling unit and system is contained in an individual cabinet 66, which is separate from the cabinet 14, and is readily connectable thereto by conduit 58, which discharges from the pumps, and conduit 68 which discharges from the water recycling system for return of wastewater to the pump unit for recycling and maintaining the liquid seal therein. Due to the fact that the discharge conduit 58 is conducting a relatively large volume of air mixed with water, the diameter thereof is much larger than the discharge conduit 68 leading from the water recycling unit or system, such differences being shown in exemplary manner, particularly in FIG. 1.

Figure 6:
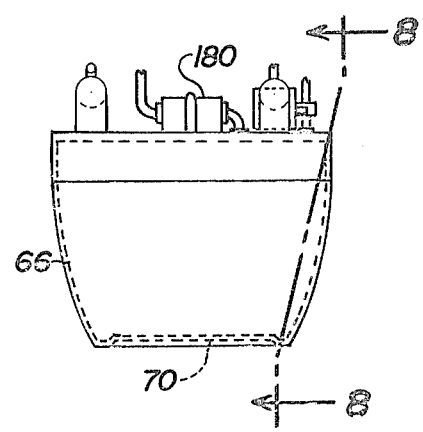
FIG. 6 is a top plan view of the cabinet shown in FIG. 5.

The cabinet 66 has a front panel 70 and adjustable feet 72 for leveling the same. Certain elements of the water recycling system project from the rear wall of the cabinet 66 as shown in FIG. 6, and also in FIG. 7, wherein the rear wall 74 is shown in cross-section. For purposes of compactness, it will be seen that the water recycling cabinet contains a lower wastewater reservoir or storage tank 76, which is surmounted by an upper fresh water reservoir or tank 78, and an air and water separator unit 80, the latter being closely adjacent one sidewall of the fresh water tank 78, as best shown in FIG. 9 and also in FIG. 7. The mixture of wastewater and air which passes through conduit 58 from the pumps enters the upper portion of the separator 80 and is directed downwardly through sleeve 82, which terminates substantially midway of the vertical separator 80 as best shown in FIG. 9. Water in the mixture passes by gravity to the lower portion 84 and from there discharges through a smaller diameter pipe 86 and downwardly extending additional pipe 88 into the lower portion of the wastewater tank 76, the bottom of which also slopes downwardly from one side toward the other, as is evident from FIG. 9. The tank 76 is supported by a pair of vertical legs 90 which respectively are disposed within vertical recesses 92 in opposite sides of the wastewater tank 76. The legs 90 are fixed to a base plate 94, as shown in FIG. 8, and the adjustable feet 72 are interconnected thereto.

Figure 8:
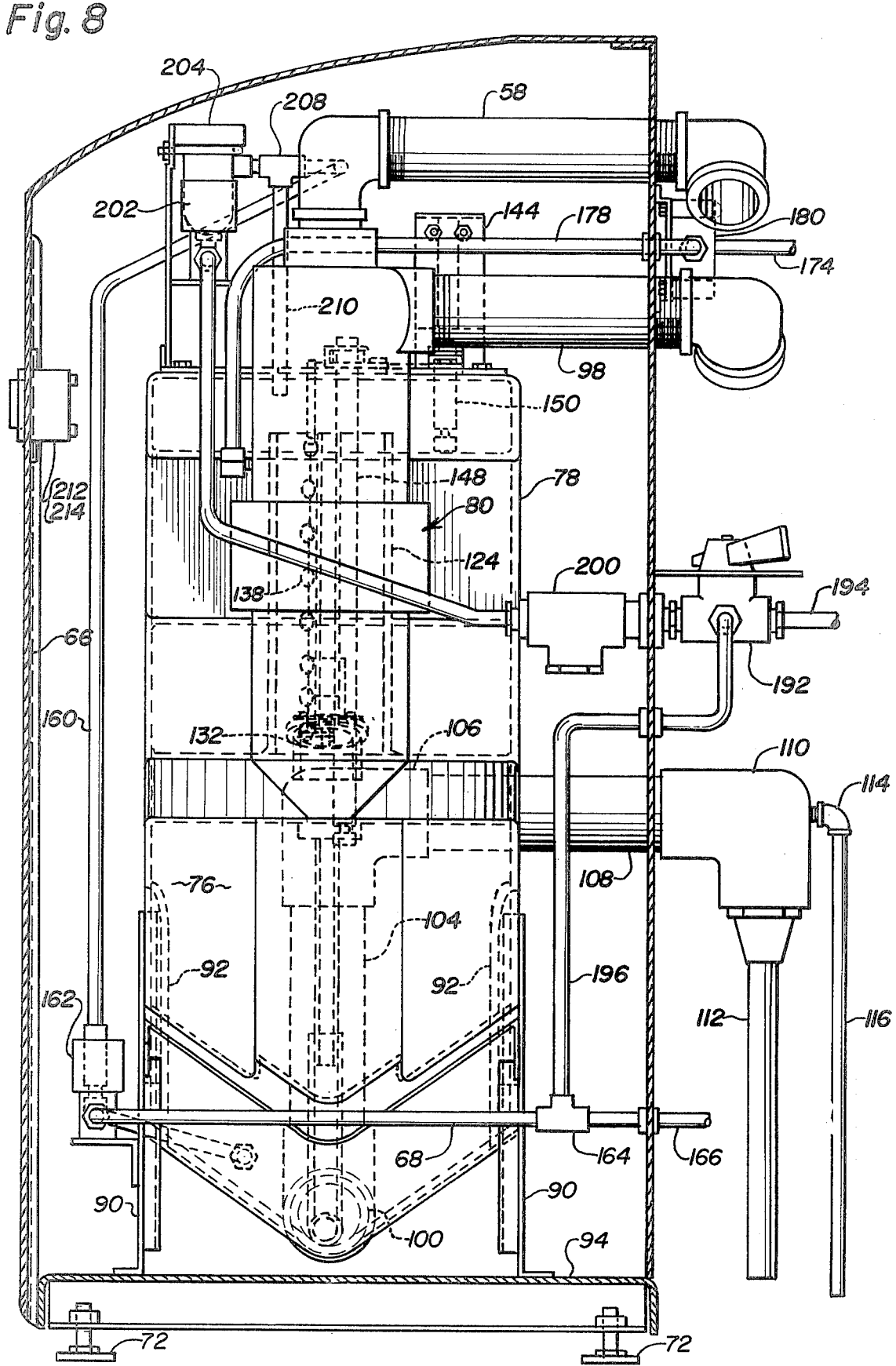
FIG. 8 is a vertical sectional view on a larger scale than employed in FIG. 6 and showing details of the system within the cabinet shown in FIG. 6, as seen on the line 8—8 thereof.
Figure 9:
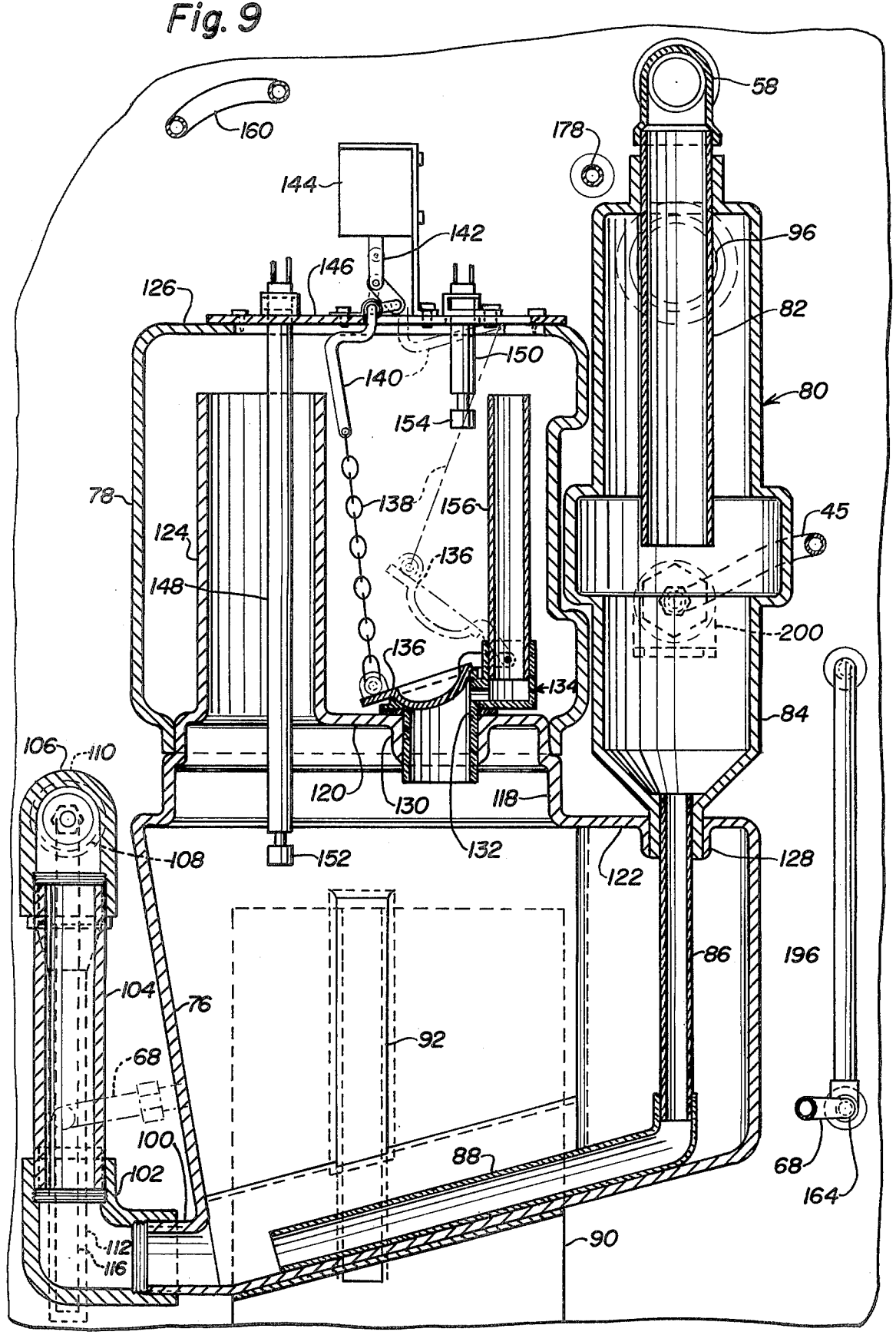
FIG. 9 is a fragmentary vertical sectional view, illustrating details of the water recycling system within the cabinet shown in FIGS. 5-8, as seen on the line 9—9 of FIG. 7.

Within the vertically elongated chamber of the separating unit 80, the air in the incoming fluid mixture readily separates from the water and discharges through a port 96 in the upper portion of the separator 80, as shown in FIG. 9, which communicates with a vent conduit 98, which is clearly shown in FIGS. 1 and 8. The vent 98 extends from the system to a stack or other venting means opening to the outdoor atmosphere.

The lowermost port of wastewater tank 76 has an outlet port 100 which, through an elbow 102, communicates with a vertical discharge pipe 104, the upper end of which is connected to another elbow 106 to which one end of a horizontal pipe 108 is connected, the opposite end being connected to a third elbow 110 from which a syphon discharge pipe 112 depends. A small branch elbow 114 communicates with the third elbow 110 and from it a syphon-breaking pipe 116 depends. The syphon discharge pipe 112 empties into an appropriate drain, such as part of the plumbing system of the building in which the operatories are located.

As best illustrated in FIG. 9, the upper portion of the wastewater storage tank 76 terminates in an upstanding neck 118 and somewhat of a closure portion 120 and a lateral extension 122 thereof at a slightly lower level. The closure portion 120 has an overflow standpipe 124, which terminates a short distance from the top 126 of the fresh water storage tank 78. Lateral extension 122 has a port 128 into which the lower portion 84 of separator 80 tightly fits. Closure portion 120 also has a port 130 into which a seat member 132 of discharge valve 134 fits. The seat 132 has a valve closure 136 which is pivotally connected at one end to the discharge valve 134 and is movable between the closed position shown in vertical section full lines and a phantom open position, clearly shown in FIG. 9. The valve closure 136 is operated by chain 138, which extends upwardly and is connected to the lower end of a crank 140 which has an upper leg interconnected by a link to the lower end of a vertically movable solenoid plunger 142, which depends from solenoid 144, the operation of which is described hereinafter.

Cover plate 146 is detachably connected to the top 126 of the fresh water tank 78 and depending from cover plate 146 is a pair of float switches 148 and 150. The float switch 148 has its lower end extending into the upper portion of the wastewater tank 76, the float 152 thereon extending into said portion of the tank. Similarly, float 154 on switch 150 extends into the upper portion of fresh water tank 78. For convenience, the float switch 148 extends downwardly through the overflow standpipe 124. It also will be seen that another standpipe 156 extends upward from the discharge valve 134 and communicates therewith for flow of fresh water through the seat member 132 for the valve closure 136.

Figure 7:
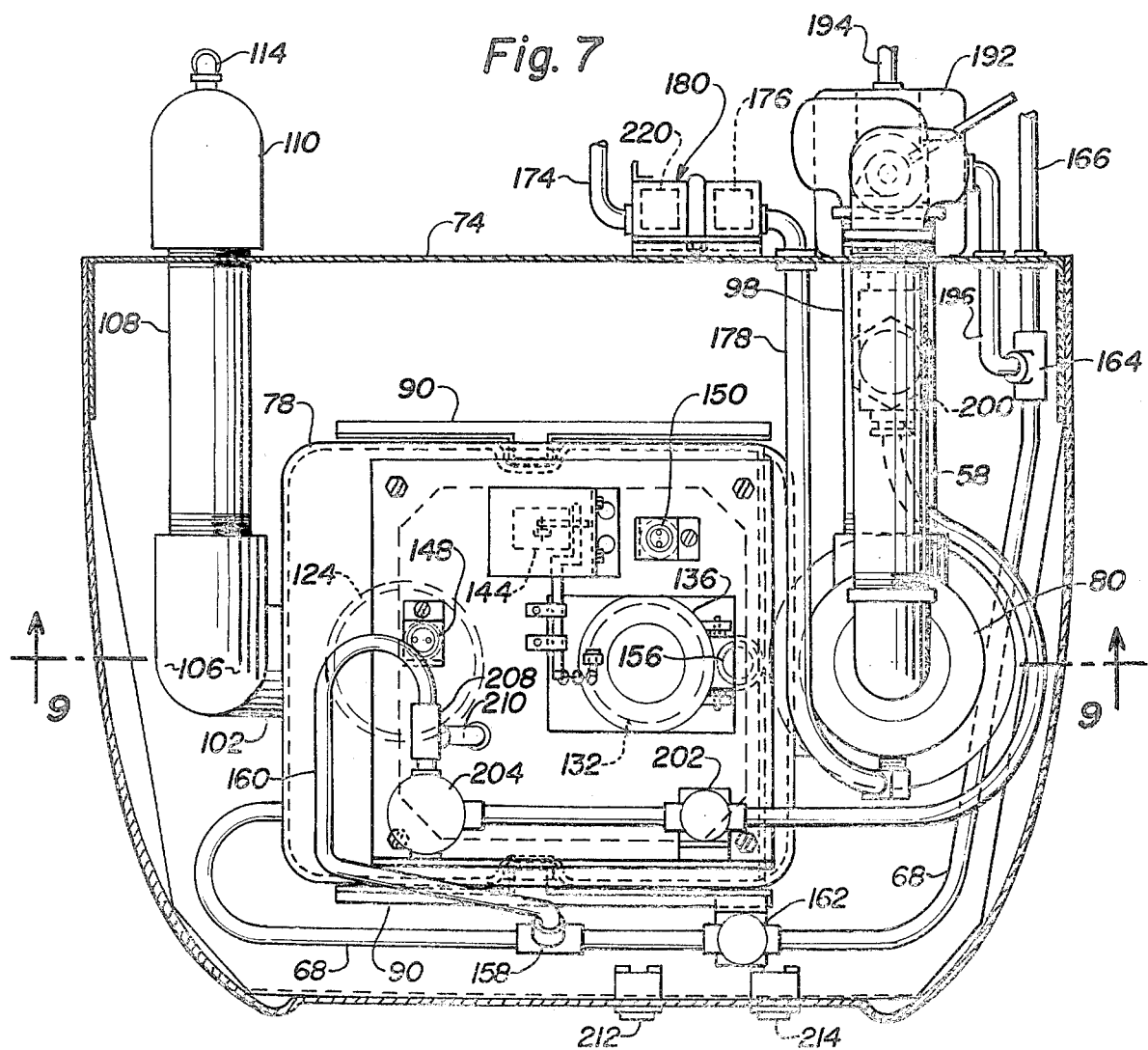
FIG. 7 is a horizontal sectional view of the contents of the cabinet shown in FIG. 5, as seen on the line 7—7 thereof and being illustrated in a larger scale than employed in FIG. 5.

Referring to FIGS. 1 and 7, the discharge conduit 68 for wastewater which leads from the lower portion of the wastewater tank 76 has a tee 158 therein for purposes of connecting fresh water inlet conduit 160 thereto. Conduit 68 then continues to a solenoid-operated control valve 162, which operates to close passage of wastewater, such as when the vacuum is shut down at the end of the day or otherwise and operates to prevent water from flowing to the pumps 10 and 12 from the bottom of the wastewater tank 76. Similarly, when closed, said valve prevents draining of the sealing water from the lower portions of the pumps 10 and 12 when the wastewater tank 76 is being drained at times described hereinafter. The conduit 68, as shown in FIG. 1, then extends upwardly to another tee 164 to which one end of a conduit 166 is connected, the opposite end being connected to the intake manifold 46 for the introduction of recycled wastewater which is distributed to the delivery conduits 48 and 50 respectively to pumps 10 and 12.

Extending from the intake manifold 46 is another conduit 168, which leads to another tee 170 to one end of which a pressure gauge 172 is connected, said tee 170 also having connected thereto, another conduit 174, which extends to a vacuum-pressure sensing switch 176 for transmission of water pressure to and from one side of a diaphragm, not shown, which is in said switch and the opposite side of said diaphragm has air pressure transmitted thereto by means of a conduit 178, the opposite end of which communicates with the interior of the air-water separating unit 80. The vacuum-pressure sensing switch 176 is within a housing 180, see FIG. 7, in which certain electrical control mechanism is contained, including a printed circuit board, not shown, which is readily insertable and replacable therein. To a certain extent, it might be considered that the mechanism in 180 that controls the operation of the recycling unit, as well as the pumping unit, is the so-called heart or brain of the control mechanism because, if all the requirements of the sensing switch 176 are satisfied, the delivery of fresh water and the recycling of wastewater will occur automatically in the following manner.

FRESH AND WASTEWATER CIRCULATING SYSTEM

Referring particularly to FIG. 1, fresh water from the city supply, for example, is connected to coupling 182 for passage through a filter 184 and thence through a pre-set regulating switch 186. The switch 186, for example, is set at the time of installation or may be varied during use for purposes of controlling a minimum pressure of fresh inlet water, which must be satisfied or else the unit automatically is shut down. Connected to the outlet of pressure-regulating switch 186 is an adjustable pressure-regulating valve 188, which controls the maximum pressure of the incoming fresh water that then passes through a vacuum breaker 190 from which the filtered and pressure-regulated fresh water then passes through to a 3-way valve 192 by means of conduit 194.

Extending between the tee 164 and 3-way valve 192 is another conduit 196 by means of which, depending upon the setting of valve 192, fresh water can be conducted through the valve 192, conduit 196 and conduit 68, into the lower portion of the waste-water tank 76, such as, for example, when the tank is to be filled at the commencement of operation on any given day or otherwise. A third port of the 3-way valve 192 is connected to still another conduit 198 for passage to another filter 200 and from there the water passes to a solenoid-operated filling valve 202, and from there to another vacuum breaker 204. Operation of the solenoid filling valve 202 is controlled by the mechanism in the housing 180 which senses the pressure in the air conduit 178, as well as the vacuum in the conduit 174, which extends from the intake manifold 46, the amount of vacuum being indicated by the vacuum gauge 172, and said vacuum can be controlled by the vacuum-control valve 54. The solenoid fill valve 202 is open when there is need for water as indicated, for example, by the float switches 148 and 150, respectively, responsive to the wastewater level in tank 76 or the level of fresh water in tank 78, while at least one of the pumps is running.

From the vaccum breaker 204, fresh water passes through conduit 206 to a tee 208, which respectively communicates with fresh water inlet conduit 160 and a supplemental fresh water conduit 210, which extends into the upper part of fresh water storage tank 78.

It will be understood that the initial and primary control for initiating movement of one or both of the vacuum pumps 10 and 12 originates in the dental cabinets or units in the dental operatory immediately associated with the various evacuating equipment, none of which are shown in the present drawings, but comprising, for example, a high-volume evacuator, a cuspidor, and a saliva ejector and multiples thereof. When, for example, the dental assistant initiates operation of a high-volume evacuator, one or both of the motors 10 and 12 start to operate. Flow of fresh water also is initiated if required by the system, due to the fresh water control solenoid valve 191 being opened by circuit means from the operatory console, not shown. Solenoid valve 191 is for pump 10 and solenoid valve 191' is for pump 12. Due to the retention of a predetermined level of wastewater effecting a seal in the lower portions of the pumps 10 and 12, priming thereof exists constantly and therefore, suction is generated by said pump which draws a vacuum in the inlet conduit 34 from the inlet port means 36 from the operatories. The mixture of wastewater and air moves through the conduit 34 to the solids separator 26 and from there to the intake manifold 46 which distributes the waste liquid and air to the pumps 10 and 12 and from which it passes through the discharge conduit 58, which is of adequate size to accommodate such mixture of air and wastewater which is passed by said conduit to the upper end of the air and water separator 80. Air is separated therein and passes to an appropriate vent through conduit 98. The wastewater separated from said mixture then falls by gravity from the lower portion 84 of separator 80 and discharges through the lower end of pipe 88 into the lower portion of wastewater tank 76.

At the start of a normal day in a dental operatory, for example, the pump unit and the water recycling unit of the overall system are readied for operation by closing an ON-OFF switch 212, if necessary, shown on the front panel 70 of the water recycling cabinet 66. An auxiliary switch 214 also is located in a similar position and is included in the circuit for purposes of effecting a manual flush of the system when desired, for emergency reasons or otherwise. Such flushing is described in detail hereinafter. Further, the central section 18 of the pump cabinet 14 has a pair of switches mounted thereon and included in the overall circuit of the system. Of these two switches, switch 216 is a double throw type switch and is operable to selectively include in readiness for operation, one or both of the pumps in the cabinet, which operation will not be initiated until one of the aforementioned instruments in the dental operatory is placed in operation. The additional switch 218 is actually an auxiliary switch for use of service personnel to start the pumps, as controlled by the setting of switch 214, irrespective of the initiation of operation of the pumps by the dental instrument in the operatory, as referred to above, whereby, service personnel can check the pump system independently of the operatory and thus, expedite servicing the unit. Thus, as a preliminary to starting the operation of the system, the ON-OFF switch 212 is placed in ON position and the pump control switch 216 is operated to place selectively either one or both of the pumps in operation. Following this, in general, operation of the pumps, as well as the recycling unit, occurs only when the various dental instruments referred to above are placed in operation in the operatory.

At the start of the aforementioned typical day in the operatory, the fresh water tank 78 is empty and the wastewater tank 76 only has a small residue of water in the lower part thereof by which the liquid seal in the lower portion of the pumps 10 and 12 is maintained so that they are continuously primed. However, as soon as one or both of the pumps start to operate, the solenoid filling valve 202 of the recycling unit is opened for purposes of introducing water to both the wastewater tank 76 and the fresh water tank 78, respectively through inlet conduit 160 for the wastewater tank 76 and conduit 210 for the fresh water tank 78. The fresh water flowing through inlet conduit 160 enters the lower portion of the wastewater tank 76 through discharge conduit 68 as shown in phantom in FIG. 9, for example.

During the aforementioned normal operation of the system, particularly at start-up time, valve 192 is in the recycling position in which fresh water flows from conduit 196 to conduit 198 and thence ultimately to the tee 208 to conduct the same respectively to the wastewater and fresh water tanks 76 and 78 as indicated above. The ON-OFF switch 212 normally is in the ON position continuously, unless for purposes of service or otherwise, it is necessary to move the switch to the OFF position. When an instrument or other suction-requiring equipment is removed from its stored position in a console, for example, control equipment on the console, operated incident to the removal of the instrument or equipment, functions to start one or both of the pumps operating, depending upon the setting of switch 216. Operation of the pump also automatically opens the solenoid valve 191, which is the principal flow control for the incoming fresh water. Solenoid-actuated filling valve 202 moves to open position, for example, in response to the sensing of the vacuum-pressure switch 176 and the diaphragm therein, which is respectively responsive on opposite surfaces thereof to the air pressure in conduit 178 from the interior of the air-water separating unit 80 and the degree of vacuum in conduit 174, which leads to the intake manifold 46. If the switch 176 senses vacuum, which indicates that the pumps are operating, such vacuum will cause solenoid-actuated valve 162 to open to direct some of the incoming fresh water to pass through conduit 68, tee 164, and conduit 166 to the intake manifold 46 and thereby supply adequate fresh water to the pump. Incidentally, the vacuum-pressure sensitive switch 176 preferably is of the type which will sense vacuum down as low as approximately two inches of water, whereby it is sensitive to almost zero vacuum.

With the filling valve 202 open, the tanks 76 and 78 will continue to fill until the float valves 148 and 150 respectively therein close the solenoid valve 202. This also will stop the flow of water to the pumps. After the flow of fresh water has been shut off as described, the pumps continue to circulate mixed air and wastewater through conduit 58 to the air and water separator 80 from which separated air passes to the vent and wastewater flows by gravity to tank 76 through the pipe 88 in the lower portion thereof. Meanwhile, the solenoid valve 162 remains open and wastewater flows by gravity through the discharge conduit 68 to the tee 164 and conduit 166 to the intake manifold 46 to delivery thereof to the pumps, thereby effecting recycling of the wastewater to achieve the economy comprising one of the principal novel features and virtues of the system comprising the present invention.

When the instruments which require suction are replaced in their stored position in the console, which is not shown, the controls actuated thereby are interconnected to the circuit in such manner that the automatic switches in the pump circuits are opened to stop the operation thereof. At this time, a timer 220, which is mounted in the housing 180, is also connected in the circuit in such a manner that said timer automatically starts to operate. Said timer is set to operate for a predetermined period, such as two hours, for example, which period is set preferably at the factory to customer's specification. If the pumps are not re-started during that period, dumping of the wastewater from the storage tank 76 is initiated by means of solenoid 144 functioning to raise the valve closure 136 from its seat in member 132, thereby causing the supply of fresh water in tank 78 to flow at a substantial rate by gravity into the wastewater tank 76 and flush the same by the head of the incoming water forcing the wastewater in tank 76 to flow through pipe 104, across pipe 108 and down pipe 112 and thereby cause a syphon action to develop which functions to drain substantially all the wastewater from the tank 76, except a small amount in the lower portion thereof at a level required in conduit 68 and other passage means extending to the bottoms of the pumps to preserve the liquid seal therein for subsequent priming of the pumps when next operated. Valve 162 closes when the pumps stop. Hence, it is closed when the syphon operation is initiated and thus, prevents the draining of water through conduit 68 and prevents filling the pumps with excess water.

The syphoning of wastewater through the discharge pipe 112 also causes discharge of some of the wastewater through the syphon-breaking pipe 116. When the wastewater tank 76 is nearly empty and air commences to flow through the discharge port 100, the syphon effect breaks and the residue wastewater in tank 76 remains as aforesaid. Otherwise, if for some reason an unusual surge of water occurs from the operatories, it will pass through the air and water separator unit 80 and into the wastewater tank 76 in a manner somewhat to flood the tank sufficiently that the syphon pipe 112 will carry off the excess over the normal full content of the tank and discharge it to drain. When the surge subsides, however, and the normal level of the wastewater in tank 76 is established, the syphon effect is broken by the syphon breaker 116 and the normal level of water in tank 76 will be maintained.

If the level of water in waste tank 76 falls below a normal predetermined amount, such as through evaporation, or otherwise, the float switch 148 senses such condition and will function through its circuit to solenoid valve 202 to cause the same to open and effect the flow of fresh water through both of the inlet conduits 160 and 210 respectively into the wastewater tank 76 and fresh water tank 78, and such flow will continue until the desired predetermined level, which is controlled by the float switch 148, is reestablished in tank 76. Then, the valve 202 will close to stop the flow of fresh water. However, the opening of the valve 202, as indicated, causes fresh water to flow into the tank 78, and if the level is above the top of the overflow standpipes 124 and 156 therein, the excess water will flow down the same into the wastewater tank 76 and thereby hasten the filling thereof to the normal level established by the float switch 148.

If any malfunction of the recycling unit occurs, it will manifest itself by the loss of vacuum in the various instruments and equipment which require it. The dentist or dental assistant will notice this, and then to permit the pumps to continue to function, the valve 192 is shifted manually to the by-pass position in which fresh water available in conduit 194, flows through the valve 192 to conduit 196, tee 164, and conduit 166, to the intake manifold 46, and thereby supplies the pumps with the necessary water to maintain the seal therein and develop the required vacuum in inlet conduit 34 from the operatories. When the valve 192 is moved to said by-pass position, the ON-OFF switch 212 of the recycling unit should be moved to OFF position and thereby de-activate the recycling unit until the malfunction can be obviated by service personnel or otherwise.

Each time the pumps stop operating, the operation of timer 220 is started. Then, if the pumps are again operated within the predetermined exemplary period for which the timer is set, the nature of said timer is such that it automatically zeros and remains so until the pumps stop. Then the timer again commences to function and continues automatically for its set period of operation.

Figure 10:
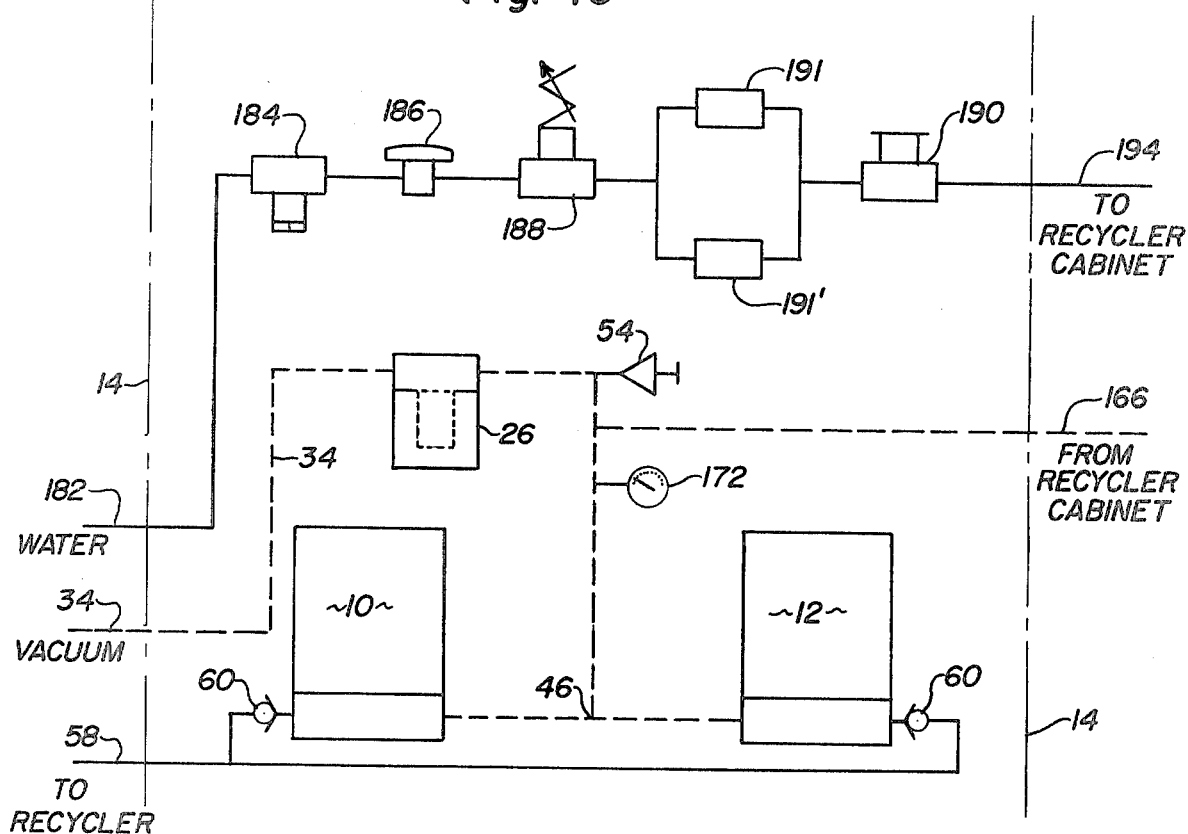
FIG. 10 is a diagram of the fluid circuitry of the pumping unit.
Figure 11:
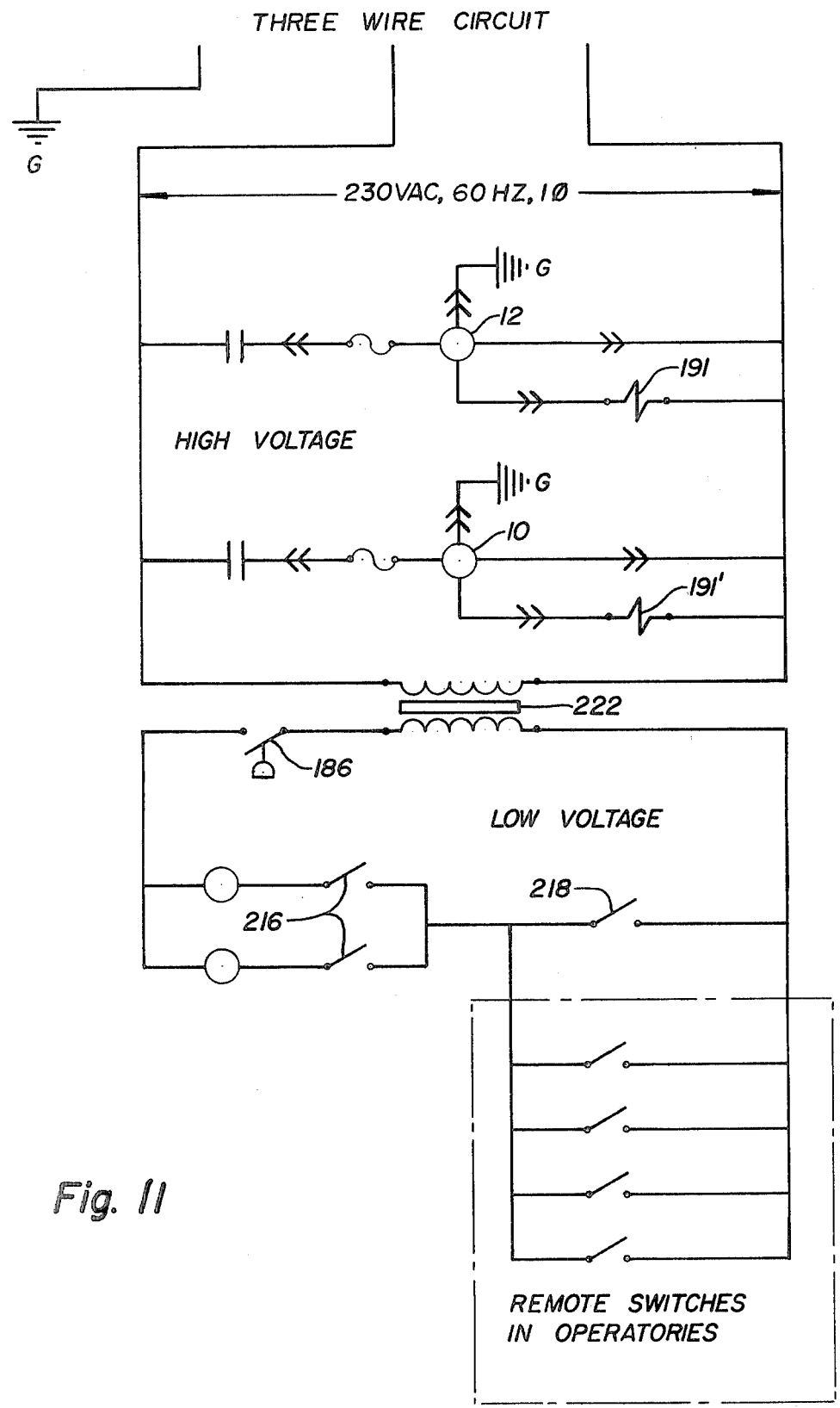
FIG. 11 is a simplified electrical wiring diagram of the pumping unit.

For purposes of facilitating at least a basic understanding of the fluid circulating and control system of the pumping unit in cabinet 14, FIG. 10 has been included in the drawings with the basic elements and apparatus associated with the fluid lines being identified by the same reference characters as in the preceeding figures. Similarly, FIG. 11 has been added to illustrate at leaast basically and briefly the electrical circuitry embodied in the pumping unit in cabinet 14. In FIG. 11, it will be seen that the remote switches in the operatories have been suitably labeled, it being understood that the switches shown diagrammatically therein correspond to switches controlled by removal and replacement of the various instruments and accessories supported in the various consoles or other equipment in the operatories, the operation of said switches basically controlling under most circumstances, the initiation of operation of the pumps 10 and 12. It also will be understood that, as described hereinabove, one or both of the pumps selectively may be placed in operation, either individually or collectively, depending upon the setting of the double-throw type switch 216, which is mounted conveniently on the front panel of the cabinet 14, as clearly shown in FIGS. 2 and 3. It also will be seen that part of the circuitry which is labeled "LOW VOLTAGE" operates, for example, at 24 volts, which is converted to that voltage by a transformer 222 from the preferred line voltage of 230 volts, which is included in the "HIGH VOLTAGE" portion of the diagram.

Figure 12:
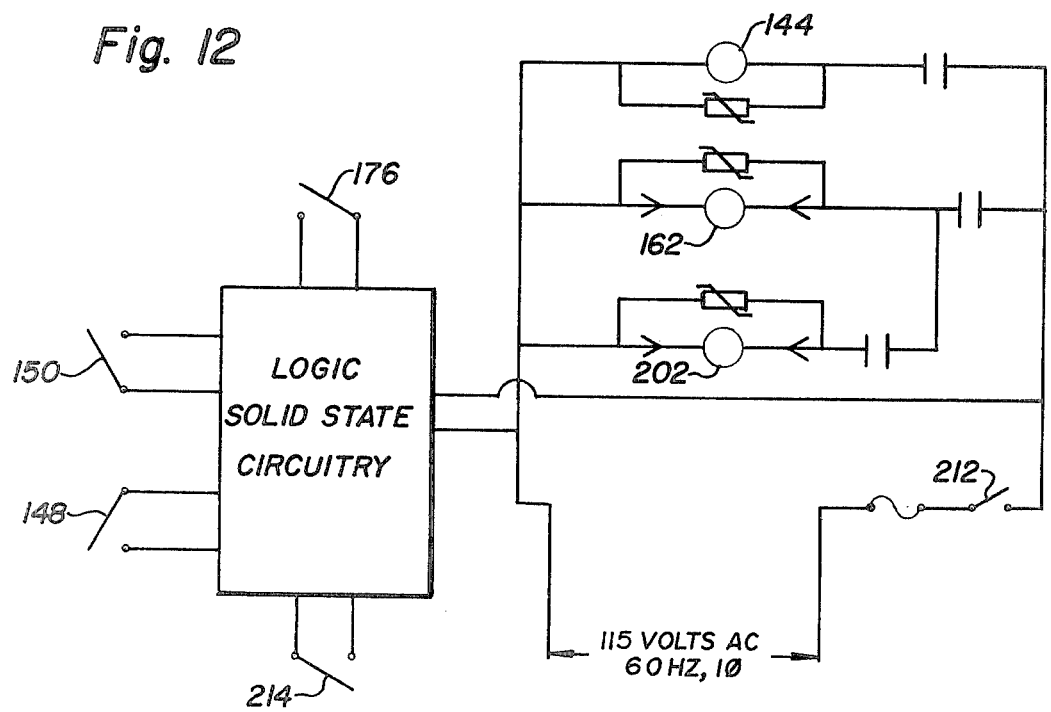
FIG. 12 is a simplified electrical wiring diagram of the recycling unit.

FIG. 12 has been added to show, at least in simplified manner, the electric circuitry of the recycling unit contained in cabinet 66 and in regard to which the block labeled "LOGIC SOLID STATE CIRCUITRY" contains non-moving electrical control elements and unit of a solid state nature, which integrate the controls for the various electrically operated devices in the circuit associated particularly with the recycling unit in cabinet 66.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. For use with dental evacuating equipment, including a water seal vacuum pump normally requiring substantial quantities of water to operate the same and discharged to waste after passing through said pump, the improvement comprising a water economizing system, including in combination, a storage tank adapted to receive wastewater pumped by said pump from said evacuating equipment, conduit means connectable to and extending from said evacuating equipment to said tank and connectable to and from said vacuum pump to recycle said water to and from said tank, vented means operable to permit air to separate from wastewater pumped from said dental evacuating equipment and means to discharge said wastewater into said tank, additional control means for said discharge means operable to maintain adequate water residue in said pump to serve as priming water therefor, timer mechanism adapted to operate said discharge means automatically after said pump has been idle for a period for which said timer has been set to function and timer control means operable to effect such operation and deactivate said timer when said pump is operating and reactivate said timer each time said pump is stopped at the completion of each evacuation operation by said pump, fresh water supply means and control means therefor operable automatically to introduce fresh water to the system at start-up and as otherwise required for makeup, and means to discharge said wastewater from said tank to a waste line or the like after a substantial period of recycling of said water by and through said vacuum pump has occurred.

2. The system according to claim 1 further including an electric solenoid type valve in a portion of said conduit means from said tank to said pump operable to close automatically when said pump is stopped to prevent flow of water from said tank to said pump and further including an electric circuit from a source of electricity to the solenoid of said valve, said circuit also being connectable to an electric motor to operate said pump which when operation is initiated produces suction in said conduit means to said pump, and said electric circuit including a vacuum-operated switch which is closed when said pump is operated and thereby closes the circuit to said solenoid valve and opens it to permit flow of water from said tank to said pump to effect said recycling of said water to and from said pump.

3. The system according to claim 1 in which said system also includes a fresh water tank having an opening connecting the same to the top of said storage tank for wastewater, said fresh water tank being compactly above said storage tank for wastewater, a flow control valve normally closing said opening, said conduit means for said storage tank for wastewater to said pump extending from the lower portion of said tank and positioned for flow by gravity to said pump to effect recycling of said wastewater, and discharge conduit means connected to the lower portion of said storage tank for wastewater and having a syphon portion extending substantially to the upper level of said storage tank and terminating below said level, and control means operable when said storage tank is to be discharged to a waste line to open said flow control valve and thereby utilize the hydraulic head of the water in said fresh water tank to force wastewater through said conduit and syphon means substantially to effect draining of said wastewater tank by syphon action and flush said tank with fresh water from the tank for fresh water.

4. The system according to claim 3 further including a flow control valve in said discharge conduit means operable automatically when said discharge of said storage tank occurs to close said discharge conduit means and thereby prevent draining of the waste water tank into pump.

* * * * *